United States Patent [19]

Sams

[11] 4,395,820

[45] Aug. 2, 1983

[54] METHOD AND APPARATUS FOR ASSEMBLING AN ELECTRODE CAP

[75] Inventor: Marvin W. Sams, Dallas, Tex.

[73] Assignee: Electrocap, Inc., Dallas, Tex.

[21] Appl. No.: 294,886

[22] Filed: Aug. 21, 1981

Related U.S. Application Data

[62] Division of Ser. No. 72,611, Sep. 12, 1979, Pat. No. 4,323,076.

[51] Int. Cl.$^3$ ............................................ H01R 43/04
[52] U.S. Cl. ...................................... 29/881; 29/453; 269/47; 269/903; 269/909
[58] Field of Search ............. 29/881, 593, 453, 281.5, 29/281.1; 128/644, 731; 324/51, 53; 269/37, 47, 52, 289 R, 903, 909

[56] References Cited

U.S. PATENT DOCUMENTS

| | | | |
|---|---|---|---|
| 1,938,375 | 12/1933 | Coffee | 269/47 |
| 3,187,745 | 6/1965 | Baum et al. | |
| 3,279,468 | 10/1966 | LeVine | |
| 3,498,291 | 3/1970 | Bunn | |
| 3,545,432 | 12/1970 | Berman | |
| 3,574,305 | 4/1971 | Muhl | |
| 3,591,118 | 7/1971 | Gentile et al. | 269/75 |
| 3,703,168 | 11/1972 | Frink | |
| 3,762,420 | 10/1973 | Moore et al. | |
| 3,998,213 | 12/1976 | Price | |
| 4,085,739 | 4/1978 | Sams | |
| 4,366,434 | 12/1982 | Ellis | 324/133 |

OTHER PUBLICATIONS

Snaith, D., Stop–Go Continuity Tester, *Radio and Electronics Constructor*, vol. 33, No. 10, Jun. 1980, Great Britain, p. 591.

*Primary Examiner*—Carl E. Hall
*Assistant Examiner*—P. W. Echols
*Attorney, Agent, or Firm*—Hubbard, Thurman, Turner & Tucker

[57] ABSTRACT

An improved biomedical electrode comprising two snap together portions which may be assembled with a layer of elastic fabric between the two portions. At least one of the portions carries a conductive electrode and a lead for making connection to a recording system. An improved electrode cap comprises an elastic cap carrying a plurality of the snap together electrodes. An improved method of assembly includes the use of a generally head shaped block having a plurality of rods extending from the surface to hold one portion of the electrodes while the elastic cap is stretched over the block so that the rods may be used for alignment of the electrode second portions with the first portions and allow the assembly to be snapped together and simultaneously permanently mounted on the cap.

6 Claims, 3 Drawing Figures

In the preferred embodiment, bushing 10 is formed from a relatively soft thermo-plastic rubber material sold under the designation Kraton 3202 by the Shell Chemical Company. Other materials, either conductive or nonconductive, may be employed for bushing 10. Relatively soft materials are preferred for greatest patient comfort. The electrode 12, in the preferred embodiment, is preferably stamped from a sheet of solid tin but other material such as silver or platinum, which are known to be useful as electroencephalographic electrodes, may be used if desired. Various elastic fabrics are well known for use in forming the basic elastic cap of the present invention. The retaining disc or retainer 14 is preferably formed from a tough relatively rigid plastic such as the ABS material which is used in the preferred embodiment.

With reference now to FIG. 2, more details of the elements of FIG. 1 are illustrated in a cross-sectional view of an assembled electrode according to the present invention. The bushing 10, conductive electrode 12, fabric 30 and retainer 14 are the same as illustrated in FIG. 1. In this preferred embodiment, the bushing 10 has an outer diameter of 0.591 inches and includes an aperture 32 in its lower portion having a diameter of 0.315 inches. The recess portion 24 provides space for both the electrode 12 and the retainer 14 and has a diameter of 0.512 inches. In the preferred embodiment, the conductive electrode 12 is 0.04 inches thick and has an outer diameter of 0.50 inches. A circular aperture 34 is provided in the center of electrode 12 and has a diameter of about 0.11 inches. In this preferred embodiment, a second smaller aperture 36 is provided at one edge of the electrode 12 and has the diameter of 0.0625 inches. The conductor 22 is attached to the electrode 12 by passing down through the second aperture 36 and soldering to the lower surface of electrode 12 at 38. In this preferred embodiment, a small cavity 40 is provided for accomodating the soldered junction 38.

The greatest diameter of retainer 14, that is, the flange 26, has a diameter of 0.48 inches while the inner diameter of the upper end 16 of bushing 10 is 0.473 inches. Thus, the retainer 14 is only slightly larger than the small diameter portion of end 16 of bushing 10. As illustrated in FIG. 2, when the retainer 14 is snapped into the electrode portion comprising bushing 10 and electrode 12, the fabric 30 is gripped between the retainer 14 and both electrode 12 and bushing 10. The fabric 30 fills the space between these parts to provide a tight grip between retainer 14 and bushing 10. Retainer 14 has an axial passageway 42 having a diameter of 0.11 inches. At some point in the assembly process, an aperture 44 is provided through fabric 30 in alignment with the apertures 34 in electrode 12 and 42 in retainer 14.

With reference now to FIG. 3, the assembly of an electrode cap according to the present invention is illustrated. A fixture, as illustrated in FIG. 3, includes a block portion 46 and a number of rods 48. The block 46 is preferably generally in the shape of a patient's head or at least in the shape of a conventional elastic cap. The elastic caps are typically manufactured from two essentially half-circle pieces of fabric joined along their circumference by a rectangular section of fabric. In similar fashion, block 46 may be fabricated from right and left half-circular sections 50 of flat material joined along their circumference by a rectangular sheet 52 bent to conform to the sections 50. For more accurate alignment of parts, the block 46 may be formed in the shape of a normal head but this is not generally believed to be necessary. In any case, the rods 48 are embedded into the block 46 at desired electrode locations. In the preferred embodiment, the electrodes are positioned to conform to the international 10/20 system as discussed in the above-referenced Price patent.

The initial step in the assembly of an electrode cap comprises placing retainers 14 on each of the rods 48. After this, an elastic cap 51 is turned inside out and stretched over the fixture comprising block 46 and rods 48. In the preferred embodiment, additional rods 53 are provided at the bottom of each side 50 for receiving a ring attached to the cap 51 for holding it on the fixture. After the cap has been placed on the fixture, the location of the rods 48 will be quite apparent. The elastic fabrics are generally somewhat transparent and, in any case, the protruding rods 48 will be quite obvious. At this point, it is desirable to cut holes through the cap 51 to allow the rods 48 to extend through the cap for receiving the bushing 10. Thus, at 54 there are illustrated several of the rods before the fabric has been cut. A hot object may be applied to the fabric over the ends of the rods 48 to melt the fabric forming a hole and allow the fabric to draw down over the rods 48 as illustrated at 56. The use of the heating element, such as a soldering iron, is believed to be preferred since it tends to seal the cut edges of the fabric and prevent unraveling. Alternatively, the outer ends of rods 48 may be provided with relatively sharp outer edges and a tight fitting cutter may be pressed over the rods to cut a circular hole from the fabric in essentially the same manner as a paper punch. In any case, once the rods 48 have been exposed as shown at 56, second portions of the electrode assembly comprising the bushing 10 and conductive electrode 12 may be placed on the rods 48. When the bushings 10 are pressed downward with sufficient force, they snap onto the retainers 14 to complete the assembly and permanently grip the elastic cap 51. The leads 22 from electrode assemblies are preferably fed through a hole 58 in the top of the cap which will lead to the outside of the cap once it is inverted back to its normal position.

In the preferred embodiment, all of the electrode leads 22 are provided in the form of a single wiring harness leading up to the hole 58 in cap 51. The individual leads 22 are, therefore, preferably fed through hole 58 from the outside of the cap before they are fed through the small holes 25 in bushings 10 and soldered to the conductive electrodes 12. A recess 60 is preferably provided in the top of block 46 for receiving the entire harness while the electrodes are assembled to the cap.

In another form of the present invention, the rods 48 are made from metal, such as steel, while the block 46 is nonconductive and preferably formed from plastic. Light emitting elements 61, such as light bulbs but preferably light emitting diodes, are provided in block 46 adjacent each of the rods 48. The light emitting elements 61 together with a source of electrical power, such as a battery, comprise a continuity tester for each of the electrodes on cap 51. A receptacle is preferably provided at the bottom of recess 60 to which the wiring harness is plugged during the assembly process. Each of the leads on the receptacle is connected to one side of the power source and the opposite side of the power source is connected to one lead of each of the light emitting devices 61. A second lead of each light emitting device is connected to a corresponding rod 48. It can be seen, therefore, that when a properly assembled electrode 12 comes into contact with a rod 48, a circuit

METHOD AND APPARATUS FOR ASSEMBLING AN ELECTRODE CAP

This application is a division of application Ser. No. 072,611, filed Sept. 12, 1979 now U.S. Pat. No. 4,323,076.

BACKGROUND OF THE INVENTION

The present invention relates to electrode caps particularly suited for use in electroencephalographic apparatus and more particularly to an improved electrode assembly and method of attaching electrode assemblies to an elastic cap.

References known to the present Applicant and believed to be relevent to the present invention include: U.S. Pat. No. 3,998,213 issued to Price on Dec. 21, 1976; U.S. Pat. No. 4,085,739 issued to the present Applicant on Apr. 25, 1978; and the publication entitled "The Promise Technology Holds for the Future of EEG Technology" by Frost, Jr., found at Pages 65 to 75 of Volume 12, No. 2 (1972) of *The American Journal of EEG Technology*. The Price patent teaches an elastic cap carrying electrodes in the international 10/20 system for use with EEG recorders. The elastic portion of the Price device comprises a series of elastic straps held together by electrode holders. The above-referenced Frost article teaches a similar cap assembled from essentially continuous stretchable fabric with a plurality of electrodes attached to the inner surface of the elastic cap. This cap is held on the patient's head by a chin strap. My above-referenced patent teaches an electrode harness arrangement by which any type of EEG cap can be held on the patient's head without inducing muscle reactions in the patient which can interfere with the proper recording of electroencephalograms.

As shown by the above references, elastic electrode caps for use with EEG's are well known and have been well accepted. Such caps greatly reduce the time required for proper application of the EEG electrodes to a patient's head by a technician. The elastic cap arrangements also reduce the possibility of movement of the electrode or loss of electrical contact during the taking of the electroencephalogram. However, as shown by these references, the electrode assemblies used in such caps have been fairly complicated.

While these elastic EEG caps have become quite popular, they remain quite expensive due to the complexity of proper assembly. In a typical fabrication process, an elastic cap is first manufactured from three or more pieces of elastic material. A pattern is then laid onto the cap and proper locations of electrodes, for example, the international 10/20 system arrangement, are marked onto the cap. A metal electrode is then typically pressed into a rubber grommet which is positioned on one side of the cap at one of the marked locations while cement is applied to the fabric. A fiber washer is usually placed on the opposite side of the fabric so that the entire assembly may then be clamped until the cement hardens to hold the electrode assembly in place. Since typically seventeen or more electrodes must be attached to the cap, it can be seen that a considerable amount of time is required to completely assemble such an electrode cap.

SUMMARY OF THE INVENTION

Accordingly, an object of the present invention is to provide an improved electrode cap for use with electroencephalographic equipment.

Another object of the present invention is to provide an improved electrode assembly which may be quickly and simply attached to an elastic cap.

Another object of the present invention is to provide improved apparatus and methods for assembly of electrode caps for electroencephalographic use.

These and other objects of the present invention are achieved by providing an improved snap together electrode assembly having first and second portions adapted for gripping an elastic fabric when snapped together. An improved method of assembly comprises placing a first portion of an electrode assembly on a first side of an elastic cap and pressing a second portion of the electrode assembly against a second side of the fabric to snap the two portions together and grip a portion of the elastic fabric therebetween. An improved fixture for assembling the electrode cap comprises a generally head shaped block having rods embedded at the desired locations of electrodes for holding first portions of the electrode assemblies while an elastic cap is stretched over the block so that the second portions of the electrodes may be pressed over the rods and onto the first portions of the electrodes.

BRIEF DESCRIPTION OF THE DRAWINGS

The present invention may be better understood by reading the following detailed description of the preferred embodiments with reference to the accompanying drawings wherein.

DESCRIPTION OF THE PREFERRED EMBODIMENTS

Figure 1:
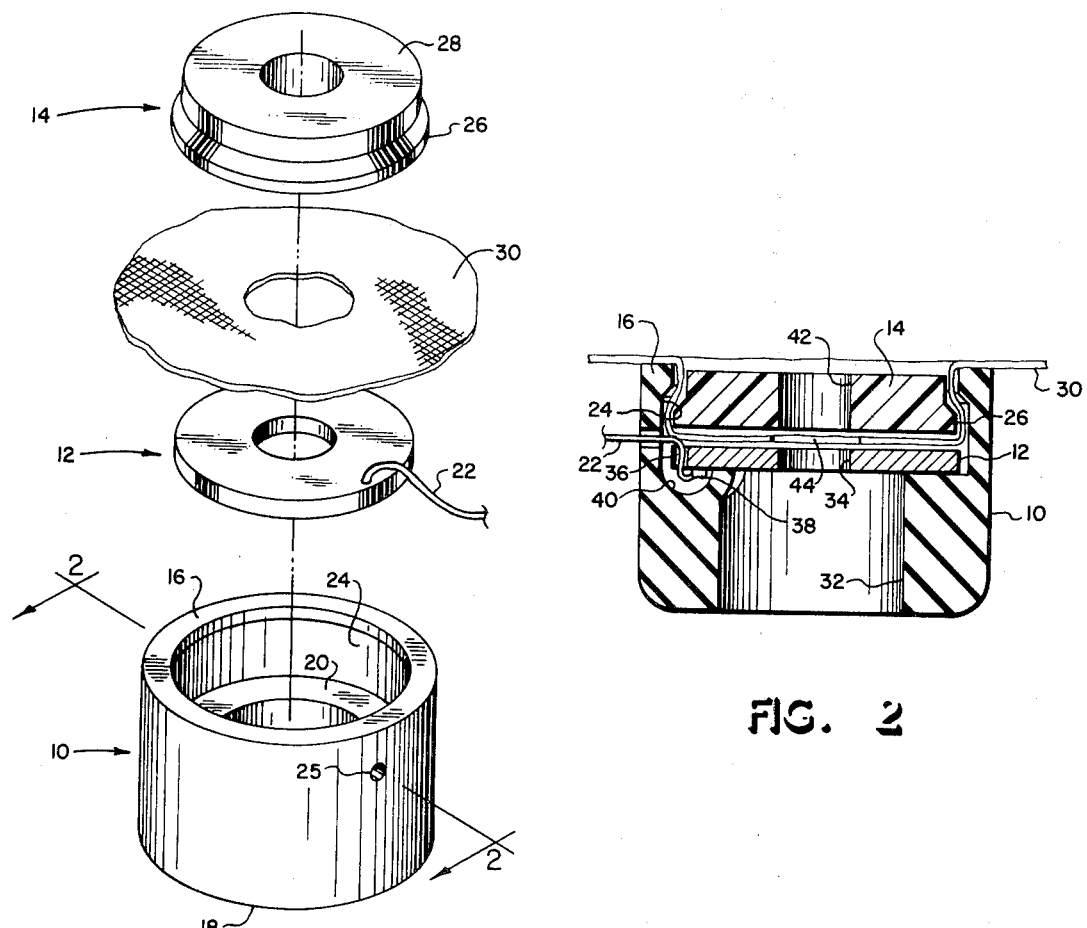
FIG. 1 is an exploded perspective view of an electrode assembly and a portion of an elastic cap according to the present invention.
Figure 2:
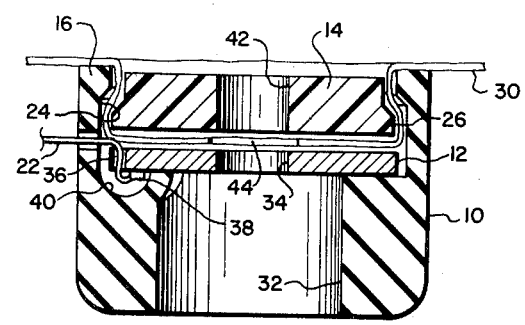
FIG. 2 is a cross-sectional illustration of an electrode assembly according to the present invention in place on a section of elastic fabric; and, FIG. 3 is a perspective view, partially broken away, of an electrode cap according to the present invention in the process of assembly on an assembly fixture.

With reference now to FIG. 1, there is provided an exploded view of a single electrode assembly for use as part of an electroencephalographic cap according to the present invention. The electrode assembly comprises primarily a rubber bushing 10, a conductive electrode 12 and a retaining disc 14. The bushing 10 is generally cylindrical and has a generally cylindrical passageway from an upper end 16 to a lower end 18. An internal shoulder 20 is provided intermediate ends 16 and 18 for supporting the electrode 12 after it is inserted through the end 16. Electrode 12 has a lead or wire 22 soldered to one edge thereof and a hole 25 is provided in the side of bushing 10 for accomodating wire 22. A recess 24 is provided at end 16 of bushing 10 for receiving the retaining disc 14. In the preferred embodiment, retainer 14 includes a lower flange 26 conforming to the shape of the internal recess 24 in the bushing 10. In this manner, an upper surface 28 of the retainer 14 may be flush with end 16 of bushing 10 after assembly. Also illustrated in FIG. 1 is a section of elastic fabric 30 shown positioned between electrode 12 and retainer 14.

is completed through the leads 22 and the light emitting device will light up indicating the continuity condition. Since the elastic fabric is typically semi-transparent, the devices 61 may be positioned behind the fabric and still be fully visible during the assembly process. If desired, the rods 48 may be formed of hollow tubes and the light emitting device may be positioned within the rods 48 so that they may be seen without interference by the fabric of cap 51.

Figure 3:
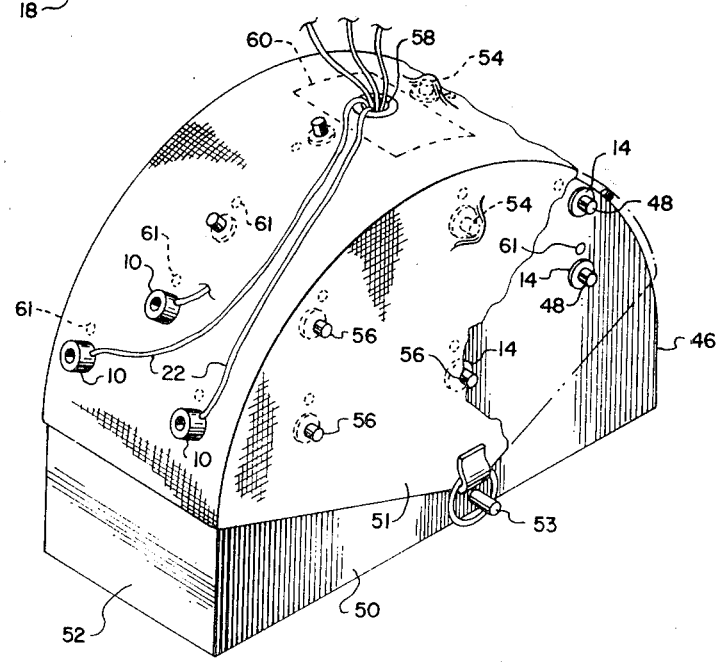

It may be desirable to assemble the electrode cap of the present invention without cutting the holes 44 in the cap fabric 30. For example, the fabric layer may desirably be used to reduce the loss of conductive gel normally used between the conductive electrode 12 and the patient's skin. Such an assembly is easily accomplished by providing rods 48 of FIG. 3 having a length corresponding to the thickness of retainers 14. The caps may then be assembled as described above except that no holes 44 need be cut in fabric 30 to allow the two electrode assembly sections to be snapped together.

Electrode caps manufactured according to the present specification are used in the same manner as those taught by the above-listed references. The cap is placed on a patient's head with the bushings 10 adjacent the scalp. The cap is preferably held in place in the manner taught by my above-referenced U.S. Pat. No. 4,085,739, although a simple chin strap may also be employed. A syringe is then used to fill the space between the patient's scalp and the conductive electrode 12 with conductive gel. A blunted needle on the syringe is preferably inserted through the apertures 42, 44, 34 and 32 in the electrode assembly and used to scrub the skin surface while gel is inserted to improve surface contact. The leads 22 from the electrode assemblies are then connected to standard electroencephalogram recording equipment. Recordings are then made in a conventional manner.

While the snap together biomedical electrode of the present invention has been shown and described with respect to electroencephalographic uses, it is apparent that the electrode has other uses. The improved biomedical electrodes may be attached to fabric holders having shapes other than the cap illustrated herein. When assembled on the appropriate holders, the electrodes may be used for recording electromyograms or electrocardiograms or any other type of biomedical electrical function. In any of these uses, the snap together feature of the present electrode allows it to be quickly and easily attached to an elastic holder shaped to provide a close fit to an appropriate body part.

While the present invention has been illustrated and described with reference to particular apparatus and methods of assembly, it is apparent that various changes and modifications can be made within the scope of the present invention as defined by the appended claims.

I claim:

1. Apparatus for assembly of an electroencephalographic electrode cap of the type comprising a generally hemispherical cap of stretchable fabric adapted to provide a close fit to a patient's head and a plurality of electrode assemblies comprising at least first and second portions having axial apertures and adapted to snap together with a portion of said fabric between said first and second portions, comprising:

a block having a shape corresponding generally to a patient's head, a plurality of rods each having a first end embedded in said block and a second end extending a short distance from said block, said rods positioned at preselected locations corresponding to desired locations of said electrode assemblies said rods receiving and locating said first portions of said electrode assemblies at said preselected locations, whereby an electrode cap may be assembled by placing said first portions of said electrode assemblies on said rods, positioning a cap over said block, and pressing said second portions of said electrode assemblies onto said rods and into snap engagement with said first portions, respectively.

2. Apparatus according to claim 1 wherein said block is electrically nonconductive and said rods are electrically conductive and said electrode assemblies each include a lead for making electrical contact to the conductive electrode, further including a continuity testing circuit having a first input connected to said rods and a second input adapted for connection to each said lead.

3. Apparatus according to claim 2 wherein said continuity testing circuit includes a light emitting device for indicating a continuous condition, and said light emitting device is carried by said block in proximity to a corresponding rod.

4. Apparatus according to claim 3 wherein said continuity circuit includes a battery having a first lead connected to a first lead of said light emitting device and a second lead connected to the electrode leads, and a second lead of said light emitting device is connected to a corresponding rod.

5. A method of assembling an electroencephalographic electrode cap of the type comprising a cap of stretchable fabric and a plurality of electrode assemblies each comprising first and second portions having axial passageways and adapted to snap together comprising:

positioning first portions of said electrode assemblies on rods carried on a block having a shape corresponding to said cap, positioning the fabric cap over the block and rods, and pressing the second portions of said electrode assemblies onto the rods and first portions to snap the first and second portions together and attach the electrode assemblies to the fabric cap.

6. The method of claim 5 further including the step of, after positioning the fabric cap on the block and rods, cutting holes in the said fabric at the locations of said rods.

* * * * *